United States Patent

Griffin, III et al.

[11] Patent Number: 5,888,577
[45] Date of Patent: Mar. 30, 1999

[54] METHOD FOR FORMING AN ELECTROPHYSIOLOGY CATHETER

[75] Inventors: Joseph C. Griffin, III, Atco; David A. Jenkins, Flanders, both of N.J.

[73] Assignee: ProCath Corporation, West Berlin, N.J.

[21] Appl. No.: 885,501

[22] Filed: Jun. 30, 1997

[51] Int. Cl.$^6$ .................................. B05D 3/00; B05D 5/12
[52] U.S. Cl. .......................... 427/2.3; 427/2.11; 427/105; 427/123; 427/534; 427/555
[58] Field of Search ..................... 427/556, 557, 427/2.11, 2.12, 2.3, 2.24, 537, 123, 105, 383.1, 534, 555

[56] References Cited

U.S. PATENT DOCUMENTS

| | | | |
|---|---|---|---|
| 5,246,576 | 9/1993 | Leader et al. | 427/125 |
| 5,378,509 | 1/1995 | Achreiner | 427/556 |
| 5,403,700 | 4/1995 | Heller et al. | 427/125 |
| 5,411,544 | 5/1995 | Mar et al. | 607/122 |
| 5,511,296 | 4/1996 | Dias et al. | 427/100 |
| 5,520,664 | 5/1996 | Bricault, Jr. et al. | 604/265 |
| 5,562,720 | 10/1996 | Stern et al. | 607/98 |
| 5,673,695 | 10/1997 | McGee et al. | 128/642 |

OTHER PUBLICATIONS

C. Paul Christensen, UV Lasers: Key Tools for Micromachining, Medical Devices & Diagnostic Industry, Jan. 1995.

*Primary Examiner*—Diana Dudash
*Attorney, Agent, or Firm*—Norman E. Lehrer

[57] ABSTRACT

A catheter has an electrically conductive material coated, deposited, or otherwise formed directly on the outer surface of the catheter. Preferably, an outer electrode is formed by ion-beam assisted deposition using a preselected metal for efficient vaporization onto the designated surface region of the catheter body. Alternatively, the electrically conductive coating may be formed by sputtering the metal onto that region of the catheter, vacuum deposition, spraying, or printing the electrically conductive material onto the entire surface region. Portions of the coating may be removed by directing a laser beam onto the outer surface of the catheter and ablating such portions. The result is an electrically conductive coating of desired thickness used to form a relatively uniform electrode throughout the desired length and surface region of the catheter body to improve the characteristics of electric field and to form an electrode which flexes to substantially the same extent as the catheter body without such a coating. As a result, the electrode does not impede the flexibility of the catheter.

5 Claims, 1 Drawing Sheet

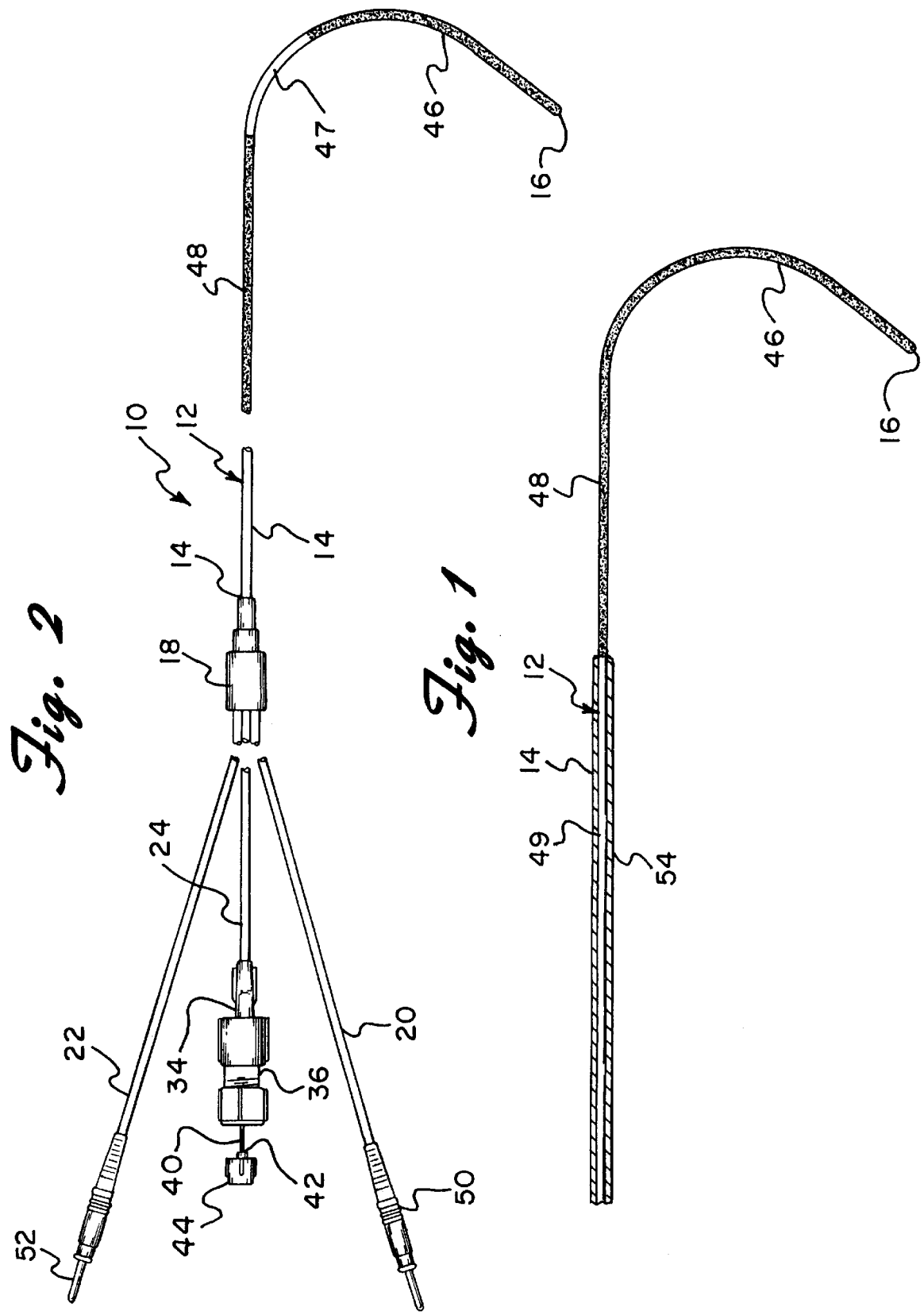

METHOD FOR FORMING AN ELECTROPHYSIOLOGY CATHETER

FIELD OF THE INVENTION

The present invention is directed toward a method for forming an electrophysiology catheter and more particularly, toward a method using a laser to form an electrode catheter with a plurality of distinct electrodes on the outer surface.

BACKGROUND OF THE INVENTION

As is well known in the art, catheters are frequently used with electrodes on the surface thereof for selectively stimulating and/or sensing electrical activity in the body and particularly in connection with the heart. For example, a catheter may be inserted into the cardiovascular system of a patient, through the superior vena cava, and into the heart so as to achieve placement of one or more electrodes in desired positions within the heart or adjacent a portion of the heart to evoke a response of the heart muscle to an electrical signal applied to the electrodes. As the utilization of catheters in remote and difficult to reach portions of the body such as the heart has increased, it has become important to be able to precisely control the movement of the catheter.

Control of the movement of catheters is somewhat difficult because of the inherent structure of the same. The body of conventional catheters is normally long and tubular. To provide sufficient control over the movement of the catheter, it is necessary that its structure be somewhat rigid. However, the catheter must not be so rigid as to prevent navigation of the catheter through the body to arrive at the precise location where the medical procedure will be performed. In addition, it is imperative that the catheter not be so rigid as to cause damage to the portions of the body through which it is being passed.

Over the years, specific catheters have also been developed for very particular purposes. For example, temporary atrial defibrillation catheters have been designed which are used specifically for terminating atrial fibrillation of a patient in a hospital or other medical facility, whether spontaneous or induced by medical procedures being performed on the patient for analytical, pre-surgical, or other purpose, such as electrophysiology tests. The catheter is coupled to an electrical waveform generator to deliver electrical shocks to the patient's heart when activated by the attending physician or surgeon after implantation of the catheter. It is desirable that such a catheter be especially amenable to rapid insertion and manueverability into proper position to limit the period during which the heart is in atrial fibrillation.

As another example, mapping and ablation catheters use an electrode array on the catheter which allows for electrically mapping areas of tissue, in the heart or otherwise, and optionally ablating certain tissue areas where pathways that cause cardiac arrhythmias are identified using one or more of the electrodes. Radio frequency electrical current is then transmitted to the tissue via the catheter which is positioned as closely as possible to the arrhythmogenic site. The electric current heats the tissue surrounding the catheter and ablates the specified tissue.

These electrode catheters are usually formed by a continuous, electrically conductive coating or layer deposited or otherwise formed directly on the outer surface of the catheter at the distal end thereof. Preferably, this outer electrode may be formed by ion-beam assisted deposition using a preselected metal for efficient vaporization onto the designated surface region of the catheter body. Alternatively, the electrically conductive coating may be formed by sputtering the metal onto that region of the catheter or by vacuum deposition, spraying, or printing the electrically conductive material on the designated surface region. The result is an electrically conductive coating of desired thickness which provides a relatively uniform electrode throughout the desired length and surface region of the catheter body to improve the characteristics of electric field and an electrode which flexes to substantially the same extent as the catheter body without such a coating. That is, the electrode does not impede the flexibility of the catheter.

The electrically conductive coating is electrically connected to a conductive lead or leads running through a lumen of the catheter by means of a conductive material in one or more openings formed in the catheter wall from the outer surface of a catheter body to the interior surface of the lumen. These openings are then filled with an electrically conductive paste which firmly contacts both the conductive coating and an exposed conductive surface of the lead. The lead is, of course, electrically insulated from other leads associated with other electrodes which may also be employed on the catheter. A single connection and, therefore, a single opening is all that is required for interconnecting the surface electrode and the internal lead.

In order to ensure that at least that the electrode is sufficiently flexible so that the same can be easily bent and again straightened, as desired, without causing any damage to the same, it is formed by a process of ion-beam assisted deposition (IBAD). This technique is described in detail in each of U.S. Pat. Nos. 5,468,562; 5,474,797; and 5,492,763, the disclosures of which are incorporated herein by reference. The use of this technique for forming an electrode catheter is also described in co-pending U.S. application Ser. No. 08/751,436. Alternatively, that co-pending application, also describes applying the electrode by sputtering, vacuum deposition, printing, or spraying. Before commencing the deposition process, areas adjacent to the location in which the flexible electrode is to be formed are masked by chemical or mechanical masking techniques. As is known in the art, the masking is removed after the deposition process is completed.

The preferred metal used in the ion-beam assisted deposition process to form the electrode is silver. However, other biocompatible low resistance metals such as gold or platinum could be utilized. The silver is vaporized and applied in a vacuum in a pure uniform coating of approximately 1 micron or less. However, the electrode could range in thickness from about 0.5 to 10 microns.

The problem with these methods however, is in the masking step, both in placing it on the catheter and removing it from the catheter once the deposition process is completed. Placing the masking on the catheter is time-consuming and may lead to inaccuracies. These catheters can be extremely small and to manually mask them is extremely tedious and may be difficult in some cases. Also, with this method, only 360° sections of the catheter can be easily masked. If a section less than 360° needs to be electrically conductive, trying to mask such an area may not only be difficult, it may lead to inaccuracies. Furthermore, removing the masking may be also be difficult, depending on the size of the catheter. Finally, the masking may not be completely removed, causing the residue to interfere with the functioning of the electrode.

SUMMARY OF THE INVENTION

The present invention is designed to overcome the deficiencies of the prior art discussed above and to provide a method for forming a catheter with an electrode deposited or coated onto the outer surface of the catheter by applying a continuous conductive coating and using a laser to remove the coating from unwanted areas of the catheter to form the electrode.

It is a further objective of the invention to provide a method which does not require masking areas of the catheter in order to prevent the electrode coating to be applied to such areas.

In accordance with the illustrative embodiments, demonstrating features and advantages of the present invention, there is provided a method for forming a catheter with a conductive electrode coating on the entire length of the outer surface of the catheter and using a laser to remove unwanted parts of the coating from that surface to form electrodes.

BRIEF DESCRIPTION OF THE DRAWINGS

For the purpose of illustrating the invention, there is shown in the accompanying drawings a form which is presently preferred; it being understood that the invention is not intended to be limited to the precise arrangements and instrumentalities shown.

FIG. 1 is a side plan view of a catheter body with a conductive coating on the outside surface of the same illustrating an initial step in practicing the present invention, and FIG. 2 is a view similar to FIG. 1 illustrating a completed catheter.

DETAILED DESCRIPTION OF THE PREFERRED EMBODIMENT

Referring now to the drawings in detail wherein like reference numerals have been used throughout the various figures to designate like elements, there is shown in FIGS. 1 and 2 a catheter constructed in accordance with the principles of the present invention and designated generally as 10. FIG. 2 illustrates a finished catheter while FIG. 1 shows the same in a prior stage of manufacture. Except in those areas which will become clear hereinafter, the catheter 10 is constructed in essentially the same manner as the electrode catheter described in co-pending U.S. application Ser. No. 08/751,436, filed on Nov. 20, 1996 entitled, "Temporary Atrial Defibrillation Catheter with Improved Electrode Configuration and Method of Fabrication" and the electrode catheter described in co-pending U.S. application Ser. No. 08/789,937, filed on Jan. 28, 1997, entitled "Focused Energy Array Ablation Catheter." The subject matter of each of these co-pending applications, assigned to the present assignee, is incorporated herein by reference.

The catheter illustrated in FIG. 2 is merely exemplary and should not be considered the only embodiment of the present invention, as will be further explained. Substantially any type of electrode catheter may be constructed utilizing the inventive concept. The figures merely depict one such catheter.

The catheter 10, as shown in FIG. 2, includes an essentially electrically insulative catheter body comprised of an elongated flexible member 12. A preferred material for producing the flexible member is extruded polyether block amid of the type sold by Atochem North America, Inc. under the trademark PEBAX. However, the flexible member 12 can be comprised of other polymeric materials which have excellent memory characteristics such as polyurethane, silicone rubber and plasticized PVC. Additionally, if desired, the flexible member 12 can be reinforced with a braided layer of stainless steel in order to increase the torsional rigidity of the same. The member 12 is preferably approximately 115 cm long and has an outer diameter of approximately 2 mm (6 French).

The member 12 has a proximal end 14 and a distal end 16. As can be seen, the area of the flexible member 12 adjacent the distal end 16 includes a substantial and continuous curve therein. This curve is preformed in the flexible member 12 in a manner well known in the art. As is also well known, the curved distal end of the flexible member 12 can be straightened if an external force is applied thereto but the same will return to its curved shape when the external force is removed.

A manifold 18 is secured around the proximal end 14 of the flexible member 12. Extending outwardly from manifold 18 are electrical leads 20 and 22 and a stylet tube 24. A central lumen is formed through the center of the flexible member 12. A plurality of additional lumina are also formed through the flexible member 12.

The end of the stylet tube 24 positioned within the manifold 18 is in communication with the central lumen. The opposing free end of the stylet tube 24 preferably terminates with a female connecting terminal 34, commonly referred to as a luer-lock hub extension. A compression fitting 36 is mated with the female connecting terminal 34. A Touhy-Borst compression fitting is preferably utilized and is available from Medical Disposables International, Inc., of West Conshohocken, Pa.

The catheter 10 also includes a stylet 40 which is slidably receivable in the central lumen of the flexible member 12. Stylet 40 is significantly stiffer than the flexible member 12 and includes a forward distal end (not shown) and a proximal end 42. The free or distal end of the stylet 40 is passed through the compression fitting 36, through the connecting terminal 34, through the stylet tube 24, and into the central lumen. The opposing end 42 of the stylet 40 extends outwardly from the compression fitting 36. The stylet 40 is preferably coated with tetrafluoroethylene (TEFLON®), is approximately 130 cm long and has a diameter of approximately 0.5 mm. The Touhy-Borst compression fitting 36 allows a physician to hold the stylet in a fixed position in a manner well known in the art.

Secured to the end 42 of the stylet 40 is an orbital knob 44. The orbital knob 44 provides a means to grasp the stylet 40 so that the stylet can be rotated and/or positioned further into or out of the flexible member 12 in order to properly position and direct the catheter. In a preferred embodiment of the invention, the stylet is straight throughout its entire length. As a result, as the stylet is moved into the flexible member 12 and enters the curved portion at the distal end thereof, the curve will tend to straighten out and eventually will be substantially colinear as the stylet 40 reaches the distal end thereof. As the stylet 40 is withdrawn from the catheter, the curved end will revert to its curved shape. It is also possible to utilize a curved stylet which, when properly moved into and out of the flexible member 12 and properly rotated, can be utilized to steer the distal end 16 of the catheter.

The flexible member 12 of the catheter 10 shown in FIG. 2 is provided with surface electrodes 46 and 48. Distal electrode 46 extends from essentially the distal end 16 of the catheter 10. A second electrode 48 is also located on the flexible member 12. Portions 47 and 49 of the flexible member 12 of the catheter do not have a conductive coating formed thereon and separate electrodes 46 and 48 from each other and from other electrodes or conductive coatings on the flexible member 12. The electrodes 46 and 48 fully encircle the outer circumference of the flexible member 12 and, in a manner to be described in more detail hereinafter, are electrically connected to the electrical connectors 50 and 52 through flexible wires that extend through lumina formed through the flexible member 12.

The electrodes 46 and 48 are interconnected to the connectors 50 and 52, respectively, by forming an opening in the outer wall of the flexible member 12 directly over the lumen carrying the flexible wire and in the area where the electrode is to be formed. A conductive adhesive bond or paste material is then inserted into each of the openings thereby forming a conductive joint to the wire. The electrode material is formed by depositing a very thin, flexible conductive coating on the surface of the catheter body in the manner described above. The conductive coating that forms the electrode electrically contacts the wire within the flexible member 12 by virtue of the conductive paste, all of which is described in detail in co-pending U.S. application Ser. No. 08/751,436.

In order to form the electrodes on the outer surface of the flexible member 12, using the present method, any form of coating, as described above, may be used; however, substantially the entire flexible member 12 may be coated with a continuous layer of the electrically conductive material. Of course, the proximal end of the flexible member 12 where no electrodes are desired may first be covered by a removable sheath 54 to prevent the application thereon of a conductive coating as shown in FIG. 1. The uncoated section 49 is shown within the sheath 54 in FIG. 1 for illustration purposes, however, the sheath 54 would also be coated with the electrically conductive material. Once the coating is completed, the sheath can be removed. Thereafter, an ultraviolet laser is used to remove the material from unwanted areas by etching.

Two different approaches may be used to remove the electrically conductive material from various sections of the catheter. The first approach is mask projection which involves using a high-energy laser to backlight a mask. The mask may be composed of a thin metal foil or several dielectric film layers which define the shape or pattern of the area to be ablated. The laser beam passes through the mask and an optical image is projected through a lens. The lens then focuses the optical image onto the outer surface of the coated catheter. When the laser beam is projected through the mask, the pattern of the area on the catheter, as defined by the mask, is ablated. Thus, a portion or portions of the coating are removed from the catheter. Using catheter 10 to illustrate, a mask defines the area 47, a laser beam passes through the mask, and the optical image of the area 47 is projected through a lens. The lens then focuses the image onto the outer surface of the flexible member 12 and the area is ablated. During the ablation process, the catheter is rotated about its axis so that conductive material can be removed around the entire 360° circumference thereof.

The second approach is direct writing which involves focusing the entire laser beam to a point and "writing" the pattern directly onto the outer surface of the coated catheter so that the laser beam is focused directly onto the catheter and portions of the electrically conductive material will be ablated. Applying this method to the catheter 10, a laser beam is focused directly onto the outer surface of the flexible member 12 of catheter 10 as the same rotates so that the area 47 of the coating is ablated. A laser such as the UV Waveguide Laser Potomac Model TGX-1000 available from Potomac Photonics, Inc. in Lanham, Md. may be used for the direct writing approach. Methods for etching using a laser are described in the article entitled: "UV Lasers: Key Tools for Micromachining" from Medical Devices & Diagnostic Industry (January 1995).

The lengths of the sections where the conductive coating is to be removed can be varied, depending upon the use, the number of electrodes needed, and the amount of space free from electrically conductive material needed. For example, if only two electrodes are needed, one at the distal tip of the catheter and one closer to the proximal end, as illustrated in FIG. 2, the coating on an area between the two electrodes may be ablated. Furthermore, if only a very small electrode is necessary, the entire flexible body is still coated and a small area can then be ablated adjacent the desired location of the electrode so that the electrode is isolated. That is, when a wire is connected to the electrode, the ablated area will prevent the entire length of the flexible body from becoming electrically conductive.

Using either of the etching methods described above will provide a catheter with one or more areas where electrodes may be formed on the outer surface of the flexible member of the catheter without the need for applying a prior art masking to the outer surface of the catheter and then removing it once the coating process is completed. Furthermore, sections of the coating may be ablated so that the electrode does not cover an entire 360° area of the flexible body. The present method is also less time-consuming, is more accurate, and is a cleaner method than the masking procedures of the prior art.

The present invention may be embodied in other specific forms without departing from the spirit or essential attributes thereof and accordingly reference should be made to the appended claims rather than to the foregoing specification as indicating the scope of the invention.

We claim:

1. A method for forming an electrophysiology catheter with an electrode coating comprising the steps of:

providing a catheter body having an elongated flexible tubular member with an outer surface having a proximal end and a distal end;

forming a coating of an electrically conductive material on said outer surface of said tubular member; and removing at least one portion of said coating intermediate said proximal and distal ends so that at least two coated portions result that are electrically insulated from one another.

2. The method for forming an electrophysiology catheter as claimed in claim 1 wherein said at least one portion of said coating is removed by a laser beam.

3. The method for forming an electrophysiology catheter as claimed in claim 1 wherein said coating is formed on said tubular member by ion-beam assisted deposition of said electrically conductive material.

4. The method for forming an electrophysiology catheter as claimed in claim 3 wherein said material is silver.

5. The method for forming an electrophysiology catheter as claimed in claim 1 further including ablating more than one portion of said coating on said tubular member so that several electrically conductive areas are formed and spaced apart from one another on said tubular member.

* * * * *